(12) United States Patent
Ammons et al.

(10) Patent No.: US 8,552,048 B2
(45) Date of Patent: Oct. 8, 2013

(54) PHOSPHORAMIDATE ALKYLATOR PRODRUGS FOR THE TREATMENT OF CANCER

(75) Inventors: Steve Ammons, Redwood City, CA (US); Jian-Xin Duan, So. San Francisco, CA (US); Donald Jung, Cupertino, CA (US); Mark Matteucci, Portola Valley, CA (US)

(73) Assignee: Threshold Pharmaceuticals, Inc., South San Francisco, CA (US)

( * ) Notice: Subject to any disclaimer, the term of this patent is extended or adjusted under 35 U.S.C. 154(b) by 775 days.

(21) Appl. No.: 12/521,290

(22) PCT Filed: Dec. 21, 2007

(86) PCT No.: PCT/US2007/088645
§ 371 (c)(1),
(2), (4) Date: Mar. 25, 2010

(87) PCT Pub. No.: WO2008/083101
PCT Pub. Date: Jul. 10, 2008

(65) Prior Publication Data
US 2010/0183742 A1    Jul. 22, 2010

Related U.S. Application Data

(60) Provisional application No. 60/871,865, filed on Dec. 26, 2006.

(51) Int. Cl.
*A01N 57/00* (2006.01)
*A01N 57/26* (2006.01)
*A61K 31/675* (2006.01)
*A61K 31/66* (2006.01)

(52) U.S. Cl.
USPC .............. 514/398; 514/94; 514/138; 514/400

(58) Field of Classification Search
None
See application file for complete search history.

(56) References Cited

U.S. PATENT DOCUMENTS

| | | |
|---|---|---|
| 3,652,579 A | 3/1972 | Hoffer et al. |
| 4,908,356 A | 3/1990 | Borch et al. |
| 4,921,963 A | 5/1990 | Skov et al. |
| 4,945,102 A | 7/1990 | Suzuki et al. |
| 5,190,929 A | 3/1993 | Borch et al. |
| 5,233,031 A | 8/1993 | Borch et al. |
| 5,270,330 A | 12/1993 | Suzuki et al. |
| 5,306,727 A | 4/1994 | Borch |
| 5,403,932 A | 4/1995 | Borch et al. |
| 5,472,956 A | 12/1995 | Borch et al. |
| 5,622,936 A | 4/1997 | Wiessler et al. |
| 5,703,080 A | 12/1997 | Nakakura et al. |
| 5,750,782 A | 5/1998 | Denny et al. |
| 5,780,585 A | 7/1998 | Anlezark et al. |
| 5,872,129 A | 2/1999 | Denny et al. |
| 5,877,158 A | 3/1999 | Bosslet et al. |
| 5,985,909 A | 11/1999 | Denny et al. |
| 6,020,315 A | 2/2000 | Bosslet et al. |
| 6,130,237 A | 10/2000 | Denny et al. |
| 6,197,760 B1 | 3/2001 | Struck |
| 6,218,519 B1 | 4/2001 | Kenten et al. |
| 6,240,925 B1 | 6/2001 | McMillan et al. |
| 6,251,933 B1 | 6/2001 | Denny et al. |
| 6,506,739 B1 | 1/2003 | Herr et al. |
| 6,656,926 B2 | 12/2003 | Borch et al. |
| 6,855,695 B2 | 2/2005 | Lin et al. |
| 6,903,081 B2 | 6/2005 | Borch et al. |
| 7,173,020 B2 | 2/2007 | Borch et al. |
| 7,304,046 B2 | 12/2007 | Borc et al. |
| 7,402,602 B2 | 7/2008 | Bigg et al. |
| 7,550,496 B2 | 6/2009 | Matteucci et al. |
| 8,003,625 B2 * | 8/2011 | Matteucci et al. .............. 514/94 |
| 2003/0008850 A1 | 1/2003 | Borch et al. |
| 2003/0050331 A1 | 3/2003 | Ng et al. |
| 2003/0096743 A1 | 5/2003 | Sender et al. |
| 2003/0130189 A1 | 7/2003 | Sender et al. |
| 2004/0121940 A1 | 6/2004 | De Groot et al. |
| 2004/0176332 A1 | 9/2004 | Borch et al. |
| 2004/0254103 A1 | 12/2004 | Lin et al. |
| 2005/0043244 A1 | 2/2005 | Lin et al. |
| 2006/0258656 A1 * | 11/2006 | Matteucci et al. ......... 514/235.5 |

FOREIGN PATENT DOCUMENTS

| | | |
|---|---|---|
| DE | 2229223 | 2/1973 |
| EP | 312 858 B1 | 2/1992 |
| EP | 648 503 A1 | 4/1995 |
| JP | 8-509727 A | 10/1996 |
| JP | 11-504009 | 4/1999 |
| JP | 2002-543059 A | 12/2002 |
| JP | 2004-515448 | 5/2004 |
| WO | WO 94/25471 A1 | 11/1994 |

(Continued)

OTHER PUBLICATIONS

Struck et al., "Antitumor activity of halogen analogs of phosphoramide, isophosphoramide, and triphosphoramide mustards, the cytotoxic metabolites of cyclophosphamide, ifofamide, and trofosfamide", CancerChem.Pharmacol., 1994, vol. 34, pp. 191-196.*
Derelanko, Toxicologist's Pocket Handbook, 2000, CRC Press, p. 16.*
Strickley, "Solubilizing Excipients in Oral and Injectable Formulations", Pharm.Res., 2004, vol. 21, No. 2, pp. 201-230.*
Berry et al., "5-Nitrofuran-2-ylmethyl group as a potential bioreductively activated pro-drug system," *J. Chem. Soc. Perkin Trans.*, 1997, 1:1147-1156.

(Continued)

*Primary Examiner* — James D Anderson
*Assistant Examiner* — Stephanie Springer
(74) *Attorney, Agent, or Firm* — Kilpatrick Townsend & Stockton LLP (57) ABSTRACT

Compositions containing, and, methods administering, TH302, are useful in treatment of cancer and other hyperproliferative diseases.

27 Claims, 3 Drawing Sheets

(56) References Cited

FOREIGN PATENT DOCUMENTS

| | | | |
|---|---|---|---|
| WO | WO 96/33198 A1 | 10/1996 | |
| WO | WO 97/39007 A1 | 10/1997 | |
| WO | 00/71134 A1 | 11/2000 | |
| WO | WO 00/64864 A1 | 11/2000 | |
| WO | WO 02/096910 A1 | 12/2002 | |
| WO | WO 03/066052 A1 | 8/2003 | |
| WO | WO 2004/085361 A1 | 10/2004 | |
| WO | WO 2004/085421 A2 | 10/2004 | |
| WO | WO 2004/087075 A2 | 10/2004 | |
| WO | WO 2005/076888 A1 | 8/2005 | |
| WO | WO 2006/057946 A2 | 6/2006 | |
| WO | 2007/002931 A2 | 1/2007 | |
| WO | WO 2008/011588 A2 | 1/2008 | |
| WO | WO 2008/076826 A2 | 6/2008 | |
| WO | WO 2008/083101 A1 | 7/2008 | |

OTHER PUBLICATIONS

Borch, RF, et al., "Antitumor activity and toxicity of novel nitroheterocyclic phosphoramidates," *J Med Chem*, 2001, 44(1): 74-77.

Borch, RF, et al., "Synthesis and evaluation of nitroheterocyclic phosphoramidates as hypoxia-selective alkylating agents," *J Med Chem*, 2000, 43(11): 2258-2265.

De Jaeger et al., "Relationship of hypoxia to metastatic ability in rodent tumours," *Br. J. Cancer*, 2001, 84(9):1280-1285.

DeGroot, et al. "Anticancer Prodrugs for Application in Monotherapy: Targeting Hypoxia, Tumor-Associated Enzymes, and Receptors," *Current Med Chem*, 2001, 8:1093-1122.

Denny et al., CAS: 133:335231, 2000.

Denny, W.A., "Nitroreductase-Based GDEPT," *Current Pharmaceutical Design*, 8(15):1349-1361 (2002).

Denny, W.A., "Prodrug strategies in cancer therapy," Eur. J. Med. Chem., 2001, 36:577-595.

Devita et al., "Cancer, Principles and Practice of Oncology," 6$^{th}$ Edition, Lippencott Williams and Wilkins, Philadelphia PA, pp. 363-376, 2001.

Duan, Jian-Xin, "Potent and Highly Selective Hypoxia-Activated Achiral Phosphoramidate Mustards as Anticancer Drugs," *J. Med. Chem.*, 2008, 51(8): 2412-2420.

Engle et al., "$^{31}$P NMR Kinetic Studies of the Intra- and Intermolecular Alkylation Chemistry of Phosphoramide Mustard and Cognate N-Phosphorylated Derivatives of N,N-Bis(2-chlorethyl)amine$^{1,2}$," *J. Med. Chem.*, 1982, 25:1347-1357.

Everett et al., "Bioreductively-Activated Prodrugs for Targeting Hypoxic Tissues: Elimination of Aspirin from 2-Nitroimidazole Derivatives," *Bioorganic Med. & Chem. Ltrs.*, 1999, 9:1267-1272.

Everett et al., "Modifying rates of reductive elimination of leaving groups from indolequinone prodrugs: a key factor in controlling hypoxia-selective drug release," *Biochemical Pharmacology*, 2002, 63:1629-1639.

Garsky Publication, "The Synthesis of a Prodrug of Doxorubicin Designed to Provide Reduced Greater Targeting Efficacy," *J. Med. Chem.* 2001, 44(24), 4216-4224. (Abstract).

Glazman-Kusnierczyk, et al. "Antitumor activity evaluation of bromine-substituted analogues of ifosfamide. 1. Stereodifferentiation of biological effects and selection of the most potent compounds," *Immunopharmacology and Immunotoxicology*, 1992, 14(4): 883-911.

Hay et al., "A 2-Nitroimidazole Carbamate Prodrug of 5-Amino-1-(Chloromethyl)-3-[(5,6,7-Trimethoxyindol-2-YL)Carbonyl]-1,2-Dihydro-3*H*-Benz[E]Indole (Amino-*Seco*-CBI-TMI) for Use With Adept and Gdept," *Biooganic Med. & Chem. Ltrs.*, 1999, 9:2237-2242.

Hay, M.P. et al., "Structure-Activity Relationships of 1,2,4-Benzotriazine 1,4-Dioxides as Hypoxia-Selective Analogues of Tirapazamine," *J. Med. Chem.*, 46(1):169-182 (2003).

Hay et al., CAS: 132:265143, 2000.

Hernick et al., "Studies on the Mechanisms of Activation of Indolequinone • Phosphoramidate Prodrugs," *J. Med. Chem.*, 46:148-154 (2003).

Hernick, et al., "Design, Synthesis, and Biological Evaluation, of Indolequinone Phosphormamidate Prodrugs Targeted to DT-diaphorase," 2002, *J. Med Chem.* 45: 3540-3548.

Kyle et al., "Direct Assessment of Drug Penetration into Tissue Using a Novel Application of Three-Dimensional Cell Culture," *Cancer Research*, 2004, 64:6304-6309.

Lee, et al., "Synthesis and Hypoxia-Selective Cytotoxicity of a 2-Nitroimidazole Mustard," Bioorganic & Med. Chem. Ltrs., 1998, 8:1741-1744.

Lin et al., "(*o*- and *p*- Nitrobenzyloxycarbobyl)-5-fluorouracil Derivatives as Potential Conjugated Bioreductive Alkylating Agents," 1986, *J. Med. Chem.*, 29:84-89.

Mauger, A.B. et al., "Self-Immolative Prodrugs: Candidates for Antibody-Directed Enzyme Prodrug Therapy in Conjunction with a Nitroreductase Enzyme," *Journal of Medicinal Chemistry*, 37(21):3452-3458 (1994).

Misiura et al., Acta Biochem. Polonica, vol. 49, 2002, p. 169-176.

Misiura et al., caplus an 2002:311287.

Naylor et al., "Recent Advances in Bioreductive Drug Targeting," *Mini Reviews in Med. Chem.*, 2001, 1:17-29.

Papot, S. et al. "Design of Selectively activated anticancer prodrugs: elimination and cyclization strategies," *Curr Med Chem Anticancer Agents*, 2002, 2(2): 155-85.

Parveen et al., "2-Nitroimidazol-5-Ylmethyl as a Potential Bioreductively Activated Prodrug System: Reductively Triggered Release of the Parp Inhibitor 5-Bromoisoquinolinone," *Bioorganic Med. & Chem. Ltrs.*, 1999, 9:2031-2036.

Rofstad et al., "Hypoxia-induced metastasis of human melanoma cells: involvement of vascular endothelial growth factor-mediated angiogenesis," *Br. J. Cancer*, 1999, 80(11):1697-1707.

Rosen et al., "Phase 1 Study of TLK286 (Telcyta) Administered Weekly in Advanced Malignancies," *Clin. Cancer Res.*, 2004, 10:3689-3698.

Steinberg, G., et al., "Synthesis and evaluation of pteroic acid-conjugated nitroheterocyclic phosphoramidates as folate receptor-targeted alkylating agents," *J Med.Chem*, 2001, 44(1): 69-73.

Stewart, D.J. et al., "Doxorubicin plus metronidazole in the treatment of recurrent or metastatic squamous cell carcinoma of the head and neck," *Am. J. Clin. Oncol.*, 16(2):113-116 (Apr. 1993), Abstract.

Struck, et al. "Antitumor activity of halogen analogs of phosphoramide, isophosphoramide, and triphosphoramide mustards, the cytotoxic metabolites of cyclophosphamide, ifosfamide, and trofosfamide," *Cancer Chemo. Pharma*, 1994, 34(3): 191-6.

Studzian, et al. "Effects of alkylating metabolites of ifosfamide and its bromo analogues on DNA of HELA cells," *Biochem, Pharm.* 1992, 43(5):937-943.

Tannock, I.F., "In Vivo Interaction of Anti-Cancer Drugs with Misonidazole or Metronidazole: Methotrexate, 5-Flurouracil and Adriamycin," *Br. J. Cancer* 42:861 (1980).

Tercel, M. et al., "Hypoxia-Selective Antitumor Agents, 16. Nitroarylmethyl Quaternary Salts as Bioreductive Prodrugs of the Alkylating Agent Mechlorethamine," *J. Med. Chem.*, 44(21):3511-3522 (2001).

Wakselman, M., "1,4- and 1,6-Eliminations from Hydroxy- and Amino-Substituted Benzyl Systems: Chemical and Biochemical Applications," *Nouv. J. Chim.*, 1983, 7(7):439-447.

West et al., "A comparison of adriamycin and mAMSA, II. Studies with V79 and human tumour multicellular spheroids," *Cancer Chemother. Pharmacol.* 1987, 20:109-114.

Workman et al., "The experimental development of bioreductive drugs and their role in cancer therapy," *Cancer and Metastasis Rev.*, 1993, 12:73-82.

Ammons et al., "Anti-tumor activity of a hypoxia activated prodrug, Th-302, in pancreatic and prostate orthotopic models of cancer," (Abstract 3985) Proceeding of the American Association for Cancer Research Annual Meeting, Apr. 2007.

Wang et al., In vivo anti-cancer efficacy of a hypoxia activated prodrug, TH-302, (abstract 3988) Proceedings of the American Association for Cancer Research Annual Meeting, Apr. 2007.

\* cited by examiner

PHOSPHORAMIDATE ALKYLATOR PRODRUGS FOR THE TREATMENT OF CANCER

CROSS-REFERENCE TO RELATED APPLICATIONS

This application is an application filed under 35 U.S.C. §371 as a national stage application of International Application No. PCT/US2007/088645, filed Dec. 21, 2007; which claims priority to U.S. Patent Application No. 60/871,865, filed 26 Dec. 2006, which is incorporated herein by reference.

BACKGROUND OF THE INVENTION

1. Field of the Invention

The present invention provides compositions and methods for treating cancer and other hyperproliferative disease conditions with hypoxia activated prodrugs alone and in combination with other anti cancer agents and therapies, and so relates to the fields of medicine, pharmacology, chemistry, and biology.

2. Background

Treating cancer is challenging because it is difficult to kill cancer cells while not affecting, or affecting to a lesser extent, normal cells. Killing or otherwise detrimentally affecting normal cells during cancer treatment can cause adverse side effects in patients. Cancer cells can differ from certain normal cells in their level of oxygenation and can be more hypoxic than normal cells. Certain agents are now in the clinic for treating cancer by targeting hypoxic cancer cells. See for example, PCT Pat. Pub. Nos. WO 00/64864, WO 04/087075, WO 07/002,931, and US Pat. App. Pub. No. 2007/0032455, each of which is incorporated herein by reference. There remains a need for compositions and methods for treating cancer. The present invention meets these needs by providing compositions and methods related to a phosphoramidate alkylator prodrug, TH302, and other such phosphoramidate alkylator prodrugs as summarized below.

BRIEF SUMMARY OF THE INVENTION

In one aspect, the present invention relates to pharmaceutically acceptable formulations comprising the compound known as TH302, or a pharmaceutically acceptable salt thereof; and a pharmaceutically acceptable carrier, excipient, or diluent. In one embodiment, the pharmaceutically acceptable formulation comprises TH302 and, as an excipient, sucrose. In another embodiment, the invention provides a stable formulation of TH302 comprising TH302 and ethanol. In various embodiments the solution comprises TH302, ethanol and not more than 5% of any other solvent, preferably not more than 2%, more preferably not more than 1%, most preferably not more than 0.5% or not more than 0.1% of a solvent other than ethanol. The formulation may be diluted (e.g., in an aqueous excipient) prior to administration to a patient. In embodiments, the present invention provides pharmaceutically acceptable formulations comprising other hypoxia activated prodrugs of phosphoramidate alkylators including, but not limited to, the compound known as TH281, and those described in WO 07/002,931. Structures of TH302 and TH281 are shown below:

In another aspect, the present invention provides a unit dose of a pharmaceutically acceptable formulation of TH302. In one embodiment, the unit dose of the pharmaceutically acceptable formulation comprises about 25 mg-about 250 mg or about 50 mg-about 150 mg of TH302. In one embodiment the unit dose comprises about 100 mg of TH302. In one embodiment, the present invention provides a unit dose formulation containing about 100 mg of lyophilized TH302. In one embodiment, the present invention provides a unit dose formulation containing TH302 (e.g., about 100 mg) in ethanol.

In another aspect, the present invention provides a method of treating cancer, by administering a therapeutically effective amount of TH302 in the range of about 4 mg/m$^2$-about 1600 mg/m$^2$, about 8 mg/m$^2$-about 800 mg/m$^2$, about 16 mg/m$^2$-about 400 mg/m$^2$, or about 32 mg/m$^2$-about 200 mg/m$^2$ to a patient in need of such treatment. In one embodiment, TH302 is administered by intravenous (i.v.) administration. In one embodiment, TH302 is administered by oral administration. In one embodiment, the therapeutically effective amount of TH302 is administered at a frequency of at least once per day, at least once per week, at least once per two weeks, or at least once per month. TH302 may be administered for a period of at least 1 week, at least 2 weeks, at least 3 weeks, or up to at least 24 weeks. In some embodiments, longer periods of administration are employed.

In one embodiment, the cancer treated is selected from breast cancer, colorectal cancer, ovarian cancer, pancreatic cancer, and prostate cancer. In another embodiment, the cancer treated is a metastatic cancer selected from the group consisting of bone marrow cancer, lung cancer, liver cancer, lymph node cancer, and ovarian cancer.

In some embodiments, TH302 is administered in combination with another anti cancer agent selected from the group consisting of cisplatin, carboplatin, docetaxel, paclitaxel, gemcitabine, and irinotecan, or is administered in combination with an anti cancer therapy such as radiation therapy.

In one embodiment, the present invention provides methods for treating cancer by administering pharmaceutically acceptable formulations of the present invention comprising hypoxia activated phosphoramidate alkylator prodrugs other than TH302, including, but not limited to, TH281, and those described in WO 07/002,931.

These and other aspects and embodiments are described in the accompanying figures and detailed description of the invention.

DETAILED DESCRIPTION OF THE INVENTION

This detailed description of the aspects and embodiments of the present invention is organized into sections as follows. Section I provides definitions of terms used herein. Section II describes the pharmaceutically acceptable formulations of the present invention. Section III provides treatment methods of the present invention. Section IV provides exemplary pharmaceutically acceptable formulations and treatment methods of the present methods. This detailed description is organized into sections only for the convenience of the reader, and disclosure found in any section is applicable to disclosure elsewhere in the specification.

I. DEFINITIONS

The following definitions are provided to assist the reader. Unless otherwise defined, all terms of art, notations, and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not be construed as representing a substantial difference over the definition of the term as generally understood in the art.

"About" refers to ±20% of a quantity and includes, but is not limited to, ±15%, ±10%, and ±5% of the quantity.

"Administering" or "administration of" a drug to a patient (and grammatical equivalents of this phrase) refers to direct administration, which may be administration to a patient by a medical professional or may be self-administration, and/or indirect administration, which may be the act of prescribing a drug. For example, a physician who instructs a patient to self-administer a drug and/or provides a patient with a prescription for a drug is administering the drug to the patient.

"Cancer" refers to leukemias, lymphomas, and other malignant tumors of potentially unlimited growth that can expand locally by invasion and systemically by metastasis. Examples of cancers include, but are not limited to, cancer of the adrenal gland, bone, brain, breast, bronchi, colon and/or rectum, gallbladder, head and neck, kidneys, larynx, liver, lung, neural tissue, pancreas, prostate, parathyroid, skin, stomach, and thyroid. Certain other examples of cancers include, acute and chronic lymphocytic and granulocytic tumors, adenocarcinoma, adenoma, basal cell carcinoma, cervical dysplasia and in situ carcinoma, Ewing's sarcoma, epidermoid carcinomas, giant cell tumor, glioblastoma multiforma, hairy-cell tumor, intestinal ganglioneuroma, hyperplastic corneal nerve tumor, islet cell carcinoma, Kaposi's sarcoma, leiomyoma, leukemias, lymphomas, malignant carcinoid, malignant melanomas, malignant hypercalcemia, marfanoid habitus tumor, medullary carcinoma, metastatic skin carcinoma, mucosal neuroma, myeloma, mycosis fungoides, neuroblastoma, osteo sarcoma, osteogenic and other sarcoma, ovarian tumor, pheochromocytoma, polycythermia vera, primary brain tumor, small-cell lung tumor, squamous cell carcinoma of both ulcerating and papillary type, hyperplasia, seminoma, soft tissue sarcoma, retinoblastoma, rhabdomyosarcoma, renal cell tumor, topical skin lesion, veticulum cell sarcoma, and Wilm's tumor.

"Hyperproliferative disease" refers to a disease characterized by cellular hyperproliferation (e.g., an abnormally increased rate or amount of cellular proliferation). Examples of hyperproliferative diseases other than cancer include, but are not limited to, allergic angiitis and granulomatosis (Churg-Strauss disease), asbestosis, asthma, atrophic gastritis, benign prostatic hyperplasia, bullous pemphigoid, coeliac disease, chronic bronchitis and chronic obstructive airway disease, chronic sinusitis, Crohn's disease, demyelinating neuropathies, dermatomyositis, eczema including atopic dermatitis, eustachean tube diseases, giant cell arteritis, graft rejection, hypersensitivity pneumonitis, hypersensitivity vasculitis (Henoch-Schonlein purpura), irritant dermatitis, inflammatory hemolytic anemia, inflammatory neutropenia, inflammatory bowel disease, Kawasaki's disease, multiple sclerosis, myocarditis, myositis, nasal polyps, nasolacrimal duct diseases, neoplastic vasculitis, pancreatitis, pemphigus vulgaris, primary glomerulonephritis, psoriasis, periodontal disease, polycystic kidney disease, polyarteritis nodosa, polyangitis overlap syndrome, primary sclerosing cholangitis, rheumatoid arthritis, serum sickness, surgical adhesions, stenosis or restenosis, scleritis, scleroderma, strictures of bile ducts, strictures (of duodenum, small bowel, and colon), silicosis and other forms of pneumoconiosis, type I diabetes, ulcerative colitis, ulcerative proctitis, vasculitis associated with connective tissue disorders, vasculitis associated with congenital deficiencies of the complement system, vasculitis of the central nervous system, and Wegener's granulomatosis.

"Patient" refers to a mammal in need of treatment for cancer. Generally, the patient is a human. A patient can be a non-human mammal such as a non-human primate, a dog, cat, cow, horse, rabbit, pig, or the like. A patient can also be a non-human animal, such as a mouse or rat, that is used in screening, characterizing, and evaluating drugs and therapies.

"Pharmaceutically acceptable carrier, excipient, or diluent" refers to a carrier, excipient, or diluent that is useful in preparing a pharmaceutical composition that is generally safe, non-toxic and neither biologically nor otherwise undesirable, and includes a carrier, excipient, or diluent that is acceptable for human pharmaceutical use as well as veterinary use. A "pharmaceutically acceptable carrier, excipient, or diluent" includes both one and more than one such carrier, excipient, or diluent.

"Pharmaceutically acceptable salt" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M., et al, "Pharmaceutical Salts", Journal of Pharmaceutical Science, 1977, 66, 1-19). Certain specific compounds of the present invention contain both basic and acidic functionalities that allow the compounds to be converted into either base or acid addition salts. The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Prodrug" refers to a compound that, after administration, is metabolized or otherwise converted to a biologically active or more active compound (or drug) with respect to at least one property. A prodrug, relative to the drug, is modified chemically in a manner that renders it, relative to the drug, less active or inactive, but the chemical modification is such that the corresponding drug is generated by metabolic or other biological processes after the prodrug is administered. A prodrug may have, relative to the active drug, altered metabolic stability or transport characteristics, fewer side effects or lower toxicity, or improved flavor (for example, see the reference Nogrady, 1985, Medicinal Chemistry A Biochemical Approach, Oxford University Press, New York, pages 388-392, incorporated herein by reference). A prodrug may be synthesized using reactants other than the corresponding drug.

"Reduction" of a symptom or symptoms (and grammatical equivalents of this phrase) refers to decreasing the severity or frequency of the symptom(s), or elimination of the symptom(s).

"Therapeutically effective amount" of a drug refers to an amount of a drug that, when administered to a patient with cancer or another hyperproliferative disease, will have the intended therapeutic effect, e.g., alleviation, amelioration, palliation or elimination of one or more manifestations of cancer or another hyperproliferative disease in the patient. A therapeutic effect does not necessarily occur by administration of one dose, and may occur only after administration of a series of doses. Thus, a therapeutically effective amount may be administered in one or more administrations.

"Treating" or "treatment of" a condition or patient refers to taking steps to obtain beneficial or desired results, including clinical results. For purposes of this invention, beneficial or desired clinical results include, but are not limited to, alleviation or amelioration of one or more symptoms of cancer or another hyperproliferative disease; diminishment of extent of disease; delay or slowing of disease progression; amelioration, palliation, or stabilization of the disease state; or other beneficial results.

II. PHARMACEUTICALLY ACCEPTABLE FORMULATIONS

In one aspect, the present invention relates to pharmaceutically acceptable formulations comprising the compound known as TH302, or a pharmaceutically acceptable salt thereof, with a pharmaceutically acceptable carrier, excipient, or diluent. TH302 is described in PCT Pat. App. Pub. No. WO 07/002,931, incorporated herein by reference. In one embodiment, the pharmaceutically acceptable formulation comprises TH302 and, as an excipient, sucrose. Such a formulation of TH302 is described in Example 1 below. In another embodiment, the pharmaceutically acceptable formulation is a solution of TH302 or a pharmaceutically acceptable salt thereof in ethanol. Such stable, ethanol formulations of TH302 are described in Example 2.

In one embodiment, the pharmaceutically acceptable formulation comprises TH281 and, as an excipient, sucrose. In another embodiment, the pharmaceutically acceptable formulation is a solution of TH281 or a pharmaceutically acceptable salt thereof in ethanol. The structures of TH302 and TH281 are shown below:

In other embodiments the present invention provides pharmaceutically acceptable formulations comprising other hypoxia activated prodrugs of phosphoramidate alkylators described in WO 07/002,931.

In another aspect, the present invention provides a unit dose of a pharmaceutically acceptable formulation of TH302. In one embodiment, the unit dose of the pharmaceutically acceptable formulation comprises about 25 mg to about 250 mg TH302, or about 50 mg to about 150 mg TH302. In one embodiment the unit dose form comprises about 100 mg of TH302. In one embodiment, the present invention provides a unit dose containing about 100 mg lyophilized TH302. A suitable unit dose pharmaceutically acceptable formulation of TH302 is described in Example 1 below.

III. TREATMENT METHODS

In another aspect, the invention provides a method of treating cancer, said method by administering a therapeutically effective amount of TH302 in the range of about 4 mg/m$^2$-about 1600 mg/m$^2$, about 8 mg/m$^2$-about 800 mg/m$^2$, about 16 mg/m$^2$-about 400 mg/m$^2$, or about 32 mg/m$^2$-about 200 mg/m$^2$ to a patient in need of such treatment. In another embodiment, TH302 can be administered to human patients in a therapeutically effective amount in the range of about 4 mg/m$^2$-about 400 mg/m$^2$, about 8 mg/m$^2$-about 200 mg/m$^2$, about 16 mg/m$^2$-about 120 mg/m$^2$, or about 32 mg/m$^2$-about 80 mg/m$^2$. Animal studies showing therapeutically effective administration of TH302 with antitumor effect are described in the Examples below (e.g., Examples 4-9). A human clinical trial protocol is described in Example 13 below.

Figure 2:
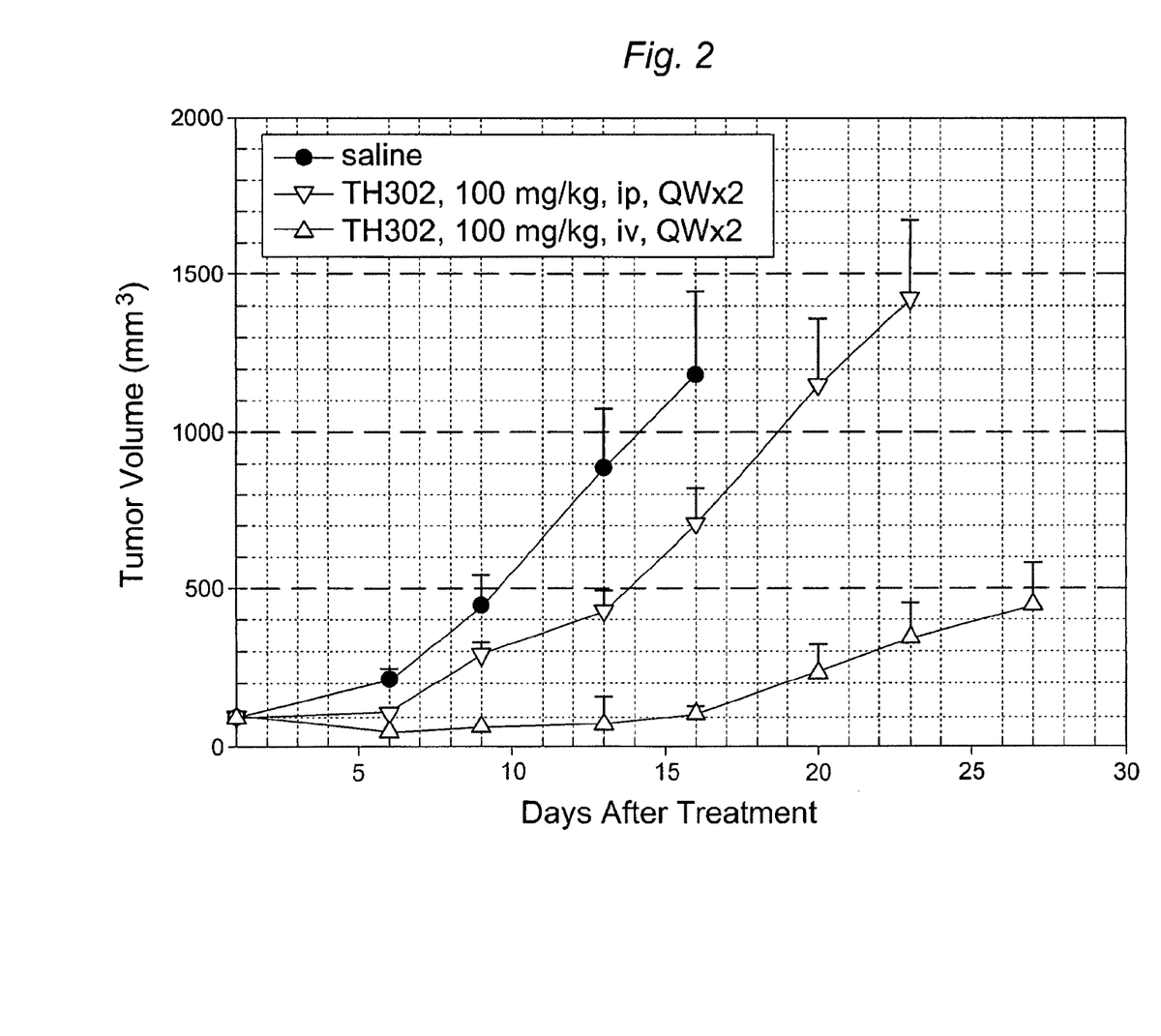
FIG. 2 shows the efficacy of intravenous administration of TH302 in treatment of cancer in a H460 xenograft tumor bearing mice.

In one embodiment, TH302 is administered by i.v. administration. Effective i.v. administration of TH302 for treatment of cancer is graphically described in FIG. 2. In one embodiment, TH302 is administered by oral administration. Efficient oral bioavailability of TH302 is described in Example 11.

In one embodiment, the therapeutically effective amount of TH302 is administered at a frequency of at least once per day, at least once per week, at least once per two weeks, up to once per month. In one embodiment, TH302 is administered for a period of at least 1 week, at least 2 weeks, at least 3 weeks, up to at least 24 weeks. In other embodiments, longer periods of administration are employed. Various frequencies and periods of TH302 administration for effective cancer treatment according to the present methods are described, for example, in Examples 4-11 and 13 below.

In one embodiment, the cancer treated is selected from breast cancer, colorectal cancer, ovarian cancer, pancreatic cancer, and prostate cancer. In another embodiment, the cancer treated is a metastatic cancer selected from the group consisting of bone marrow cancer, lung cancer, liver cancer, lymph node cancer, and ovarian cancer.

In one embodiment, TH302 is administered in combination with another anti cancer agent selected from the group consisting of cisplatin, carboplatin, docetaxel, paclitaxel, gemcitabine, or irinotecan. In one embodiment, TH302 is administered in combination with an anti cancer therapy such as radiation therapy. Administration of TH302 in combination with another anti cancer agent or an anti cancer therapy is described, for example, in Examples 4-9 below.

In particular embodiments the invention provides a method of treating a patient with prostate cancer by administering a therapeutically effective amount of TH302 (e.g., in the range of about 4 mg/m$^2$ to about 1600 mg/m$^2$) to the patient. In one embodiment the patient is also treated with docetaxel.

In another particular embodiment the invention provides a method of treating a patient with metastatic cancer by administering a therapeutically effective amount of TH302 (e.g., in the range of about 4 mg/m$^2$ to about 1600 mg/m$^2$) to the patient. In one embodiment the patient is also treated with irinotecan.

In one embodiment, the present invention provides methods for treating cancer administering pharmaceutically acceptable formulations of the present invention comprising hypoxia activated phosphoramidate alkylator prodrugs other than TH302, including, but not limited to, TH281, and those described in WO 07/002,931.

The invention, having been described in summary and in detail, is illustrated but not limited by the Examples below that provide pharmaceutically acceptable formulation of TH302 of the present invention and demonstrate the efficacy of TH302 administration to treat cancer in accordance with the present methods.

IV. EXAMPLES

Example 1

A Lyophilized Unit Dose Formulation of TH302

A solution (20 mL) of TH302 (100 mg) and sucrose (1 g) was added to a lyophilization vial and lyophilized to yield a lyophilized unit dose form of TH302. For purposes of human administration, an unit dose form was dissolved in DW5 and an appropriate amount of this solution administered to patients.

Example 2

An Ethanol Formulation of TH302

TH302 was dissolved in absolute ethanol to yield a pharmaceutically acceptable liquid formulation of 5% TH302. As used herein, a 5% solution of TH302 contains 5 g of TH302 in 100 mL of the solvent (e.g., ethanol).

The stability of an ethanol formulation of TH302 was demonstrated as follows. A liquid formulation of TH302 in ethanol was prepared containing 1 mg TH302 in 1 mL of the solution. Aliquots were withdrawn from this formulation and diluted with ethanol to yield a 40 μg/mL formulation of TH302 in ethanol, which was incubated at 20° C. and 37° C. and the stability analyzed by high performance liquid chromatography (HPLC). The HPLC employed the following components and conditions: column (Alltech, Alltima C18, 50×4.6, 3 μm), mobile phase (water and acetonitrile), flow rate 0.8 mL/min, injection volume (10 μL), detection (UV detection at 325 nm and 254 nm), and column temperature (room temperature). The composition of the mobile phase was as tabulated below:

| Time (min) | water % | Acetonitrile % |
|---|---|---|
| 0.01 | 95 | 5 |
| 4.5 | 5 | 95 |
| 7.0 | 5 | 95 |
| 8.0 | 95 | 5 |
| 11.0 | 95 | 5 |

The stability results are tabulated below:

| TH302 formulation | TH302 (%) | |
|---|---|---|
| incubated (Days) | 37° C. | 20° C. |
| 0 | 96.97 | 96.97 |
| 3 | 96.95 | 96.98 |

-continued

| TH302 formulation | TH302 (%) | |
|---|---|---|
| incubated (Days) | 37° C. | 20° C. |
| 5 | 96.98 | 96.91 |
| 7 | 96.98 | 96.96 |
| 10 | 96.30 | 96.95 |
| 14 | 96.01 | 96.98 |
| 24 | 95.46 | |

The results demonstrate that under the test conditions, a solution of TH302 in ethyl alcohol was stable at 20° C.

Example 3

Demonstration of Methods of Synthesizing and/or Purifying TH302

TH302 can be synthesized and separated from unwanted reaction material as described in Examples 6, 8, and 22-26 of PCT Pat. App. Pub. No. WO 07/002,931 (incorporated herein by reference). Eluents useful in separating TH302 by column chromatography include the acetone/toluene based eluent described in Example 6 of PCT Pat. App. Pub. No. WO 07/002,931, supra, and 5% Hexane/ethyl acetate-5% MeOH/ethyl acetate. In accordance with these methods, API grade TH302 was manufactured by Syngene, India. These synthetic methods can be modified as described below. $POBr_3$ can be used as the phosphorylating agent instead of $POCl_3$. When $POCl_3$ is used as a phosphorylating agent, the hydrolysis of the intermediate, $ClP(=O)(NHCH_2CH_2Br)_2$ (1 equivalent), can be performed using an aqueous NaBr (10 equivalent) solution.

Example 4

Demonstration of TH302 Efficacy For Treatment of Cancer in Combination with Irinotecan TH302 and irinotecan (CPT-11) were formulated as follows: TH302 (7.5 mg/mL) in saline and CPT-11 (5 mg/mL) in 2% Tween80-saline. The formulations were filtered through a 0.2 μm filter then delivered to animals within one hour after it was made. HT29 Human colorectal cancer cells were prepared in 50% matrigel and 50% RPMI 1640 medium and implanted ($3\times10^6$ cells) in the subcutaneous space of the right flank of 90 mice (0.2 mL/mouse). Tumor volumes reached about 160 mm³ on day 12 day post implantation. Seventy two animals with similar tumor size were chosen for treatment after randomization. The remaining mice were used as no treatment control.

The mice were administered TH302 intravenously at 75 mg/kg, once per week for 2 weeks (Q7D×2, i.v.) alone, and in combination with CPT-11, administered at, 50 mg/kg, (Q7D× 3, intraperitoneally (i.p.)). None of the treatment groups of mice demonstrated unexpected body weight loss. After dosing started, tumor volumes were measured twice per week. On day 29, there was 59% tumor growth inhibition of tumors on the mice undergoing the combination treatment compared to that of the control mice administered vehicle (5% DMSO, 5% Tween80-D5W, 2% Tween80-saline). For the mice administered CPT-11 alone, i.e., those on CPT-11 monotherapy, 41% tumor growth inhibition was observed compared to the control group of mice.

A dose effective for human administration can be estimated from a mouse dose by dividing the mouse dose by 12.3. Thus, in one embodiment, of the present invention, TH302 can be administered to humans for treating cancer in an amount of about 75/12.3 mg/kg or about 6 mg/kg. A human dose in mg/kg can be converted to mg/m² by multiplying the mg/kg dose by 40. Thus, in one embodiment, of the present invention, TH 302 can be administered in an amount of about 240 mg/m² to human for treating cancer. Using the same conversion factor, doses of TH302 effective in treating cancer in humans can be estimated from the effective doses obtained for mice as described in Examples 2-9.

Example 5

Demonstration of TH302's Efficacy to Treat Ovarian Cancer

Forty nude mice were subcutaneously implanted with IGROV1 human ovarian cancer cells ($5\times10^6$ cells/mouse). The tumor volumes were measured twice weekly starting on day 7. On day 8, tumor volumes reached about 97.7±3.9 mm³. The mice were randomized in 3 treatment groups that were administered the following: CDDP (4 mg/kg, ip, Q7D×2), CDDP (6 mg/kg, i.p. Q7D×2), and TH302 (75 mg/kg, i.v., Q7D×2). A control group of mice were administered saline. While treatment with CDDP at both doses did not show significant reduction in tumor volume, TH302 treatment demonstrated significant growth inhibition (P<0.05). Forty five days after the first administration of TH302, tumor growth inhibition was 66%. The tumor growth delay (to 300 mm³) was 19 days. The mice showed body weight gain during the treatment period demonstrating that the administration of TH302 was safe at the amount administered. This example demonstrates the efficacy of TH302 alone, i.e., as a monotherapy, for treating ovarian cancer.

Example 6

Demonstration of TH302's Efficacy to Kill Hypoxic Tumor Cells

H460 human non small cell cancer (NSCLC) cells were prepared in 30% or 50% matrigel in PRIM medium. Then $2\times10^6$ cells suspended in 50% matrigel were implanted subcutaneously in the right flank in 35 mice (0.2 mL/mouse), $0.5\times10^6$ cells suspended in 30% matrigel were similarly implanted in 30 mice. Mice bearing similar sized tumors, preferably ~300 mm³ were selected for TH302 administration. TH302 was formulated in saline and a single dose administered intravenously at 50 mg/kg.

The mice were placed in 95% and 10% $O_2$ chamber for 30 min before the dosing and returned to the chamber for 2 hours immediately after treatment. Twenty-four hours post treatment, tumors were removed. The tumor tissue was minced and obtain single cells were obtained by digesting the minced tissue with an enzyme cocktail for 15 min at 37° C. with stirring, and filtering through a 40 μm sterile mash. Cell numbers were counted by a coulter counter. After a serial dilution, the ells were placed in a 60 or 100 mm Petri dish and incubated at 37° C. for 8 to 10 days for the colonies to form. The colonies were counted after stained with crystal violet (0.25% in 95% ethanol). The plating efficiency (PE) was calculated by dividing the number of colonies formed by the number of cells seeded. The surviving fraction (SF) was calculated by dividing as the PE of treated cells by PE of the cells from saline control.

Figure 1:
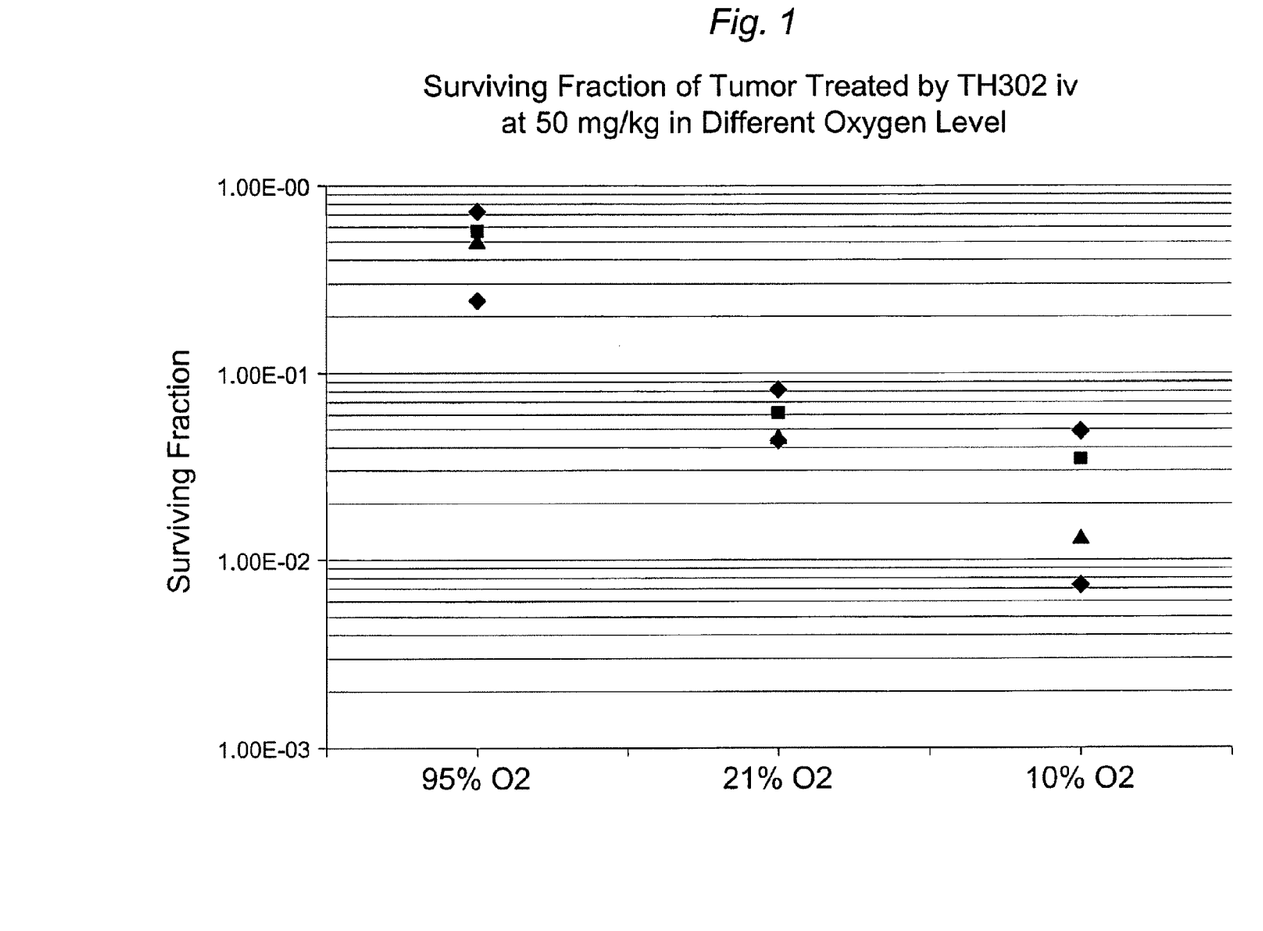
FIG. 1 shows the surviving fraction (SF) of tumors following treatment with 50 mg/kg TH302 under different level of oxygen concentration. See Example 6, infra. Different symbols represent individual animals.

The results are described in FIG. 1 below. The tumor cells obtained from tumors of mice breathing 95% $O_2$ demonstrated the highest SF. The mean SFs were 5.76%, 2.58%, and 50.38% for tumor cells obtained from tumors of mice breathing 21% $O_2$, 10% $O_2$ and 95% $O_2$ respectively. The results demonstrate that, in vivo, with increasing hypoxia, TH302's anti tumor efficacy increases.

Example 7

Demonstration of TH302's Efficacy to Treat Orthotopically Implanted Prostate Tumors This experiment demonstrates the efficacy of TH302, in treating PC-3 human prostate tumor that was orthotopically implanted in mice. Orthotopically implanted tumors are invasive and kill untreated tumor bearing animals. In the green-fluorescent protein (GFP) PC3 prostate orthotopic model, the experiment was performed in a manner similar to that described in Example 55 of WO 07/002,931 (incorporated herein by reference), and, Taxotere® (12 mg/kg), instead of gemcitabine, was administered once a week for two weeks. Administration of TH302 resulted in a tumor growth delay (TGD) of 16 days, and a reduction in tumor volume of 84% when compared to the final measurements in the vehicle group (day 31). Administration of Taxotere® alone resulted in a TGD of 31 days and a regression of tumors to 21±15 mm$^3$ whereas tumors treated with TH302 in combination with Taxotere® regressed to 16±8 mm$^3$. Tumors of mice undergoing the combination treatment never reached a volume of 500 mm$^3$. Beyond day 31, Taxotere® treated tumors began to grow, reaching a volume of 766 mm$^3$ on day 62. Tumors of mice undergoing the combination treatment demonstrated better prognosis compared to the Taxotere® alone treatment, and reached a volume of 180 mm$^3$ (P<0.01 vs Taxotere® alone). 4 of 8 mice treated with a combination of TH302 and Taxotere® demonstrated no detectable GFP expression and were considered to be cured. These results demonstrated that TH302 in combination with chemotherapy was effective in treatment of and curing cancer.

Example 8

Demonstration of the Anti-metastatic Cancer Efficacy of TH302

This example demonstrates the efficacy of TH302 in treating micrometastases in bone and soft tissue when administered in combination with Taxotere® (Docetaxel, Sanofi Aventis). Male nude mice were injected into their left ventricle with PC-3 human prostate cells (3×10$^6$) transfected with the gene for luciferase. The success of the intracardiac transfections was verified by a bioluminescence scan after the injection. On day 14, the mice with established bone tumor burden were randomized into four treatment groups (N=10): Taxotere® alone (20 mg/kg once a week for three weeks, i.v.), TH302 alone (50 mg/kg daily, 5 days a week for 3 weeks), combination treatment with both agents, and vehicle. Bioluminescence imaging was performed under anesthesia using an IVIS 50 optical imaging system.

Bone and soft tumor burden (primarily lungs and liver) increased with time, about 1000 fold, in the vehicle group. All vehicle-treated mice lost weight from disease progression and died by 29 days after treatment initiation. Mice treated with TH302 alone demonstrated a significant reduction of bone metastases (94%) and soft tissue tumor burden (95%) by the end of the study (day 43). There was minimal weight loss suggesting an overall reduction in disease progression. Mice treated with Taxotere® alone exhibited significant reduction in bone metastases and soft tissue tumor burden compared to vehicle. Taxotere® treatment, on average, prevented disease progression for most of the study and resulted in some regressions but resulted in weight loss and a toxicity-related death.

Combination treatment was associated with a surprising, continued reduction in bone metastases and metastatic soft tissue tumor burden beyond the period of dosing. All bioluminescence had disappeared by day 29 and remained at zero until the end of the study. Toxicities in the combination group were similar to those observed in the Taxotere® group. Thus, TH302 demonstrated no toxicity beyond Taxotere® related toxicities. H&E staining of samples from the vehicle group demonstrated large metastatic foci protruding through the bone whereas animals treated with the combination therapy exhibited a morphology with few, if any, visible tumor cells.

These results demonstrate that TH302 alone is effective in this aggressive lethal model of prostate metastatic disease. Combining TH302 with Taxotere® was effective, eradicating metastases in bone and soft tissues as measured. Therefore, a combination of TH302 and Taxotere® can be useful for treatment of metastatic disease associated with prostate cancer.

Metastatic tumors were also grown in mice by injecting H460 NSCLC cancer cells into the pleural cavity. Metastases were observed among other organs in the lungs and ovary. Treatment of these metastatic tumor bearing mice with TH302 alone (Q3D×5, 100 mg/kg, i.v.) demonstrated a visible reduction in metastatic tumor mass. Thus, TH302 is effective in treatment of metastatic tumors, when administered alone and in combination with another anti cancer agent.

Example 9

Demonstration of TH302's Efficacy to Treat Cancer in Combination with Radiation

Figure 3:
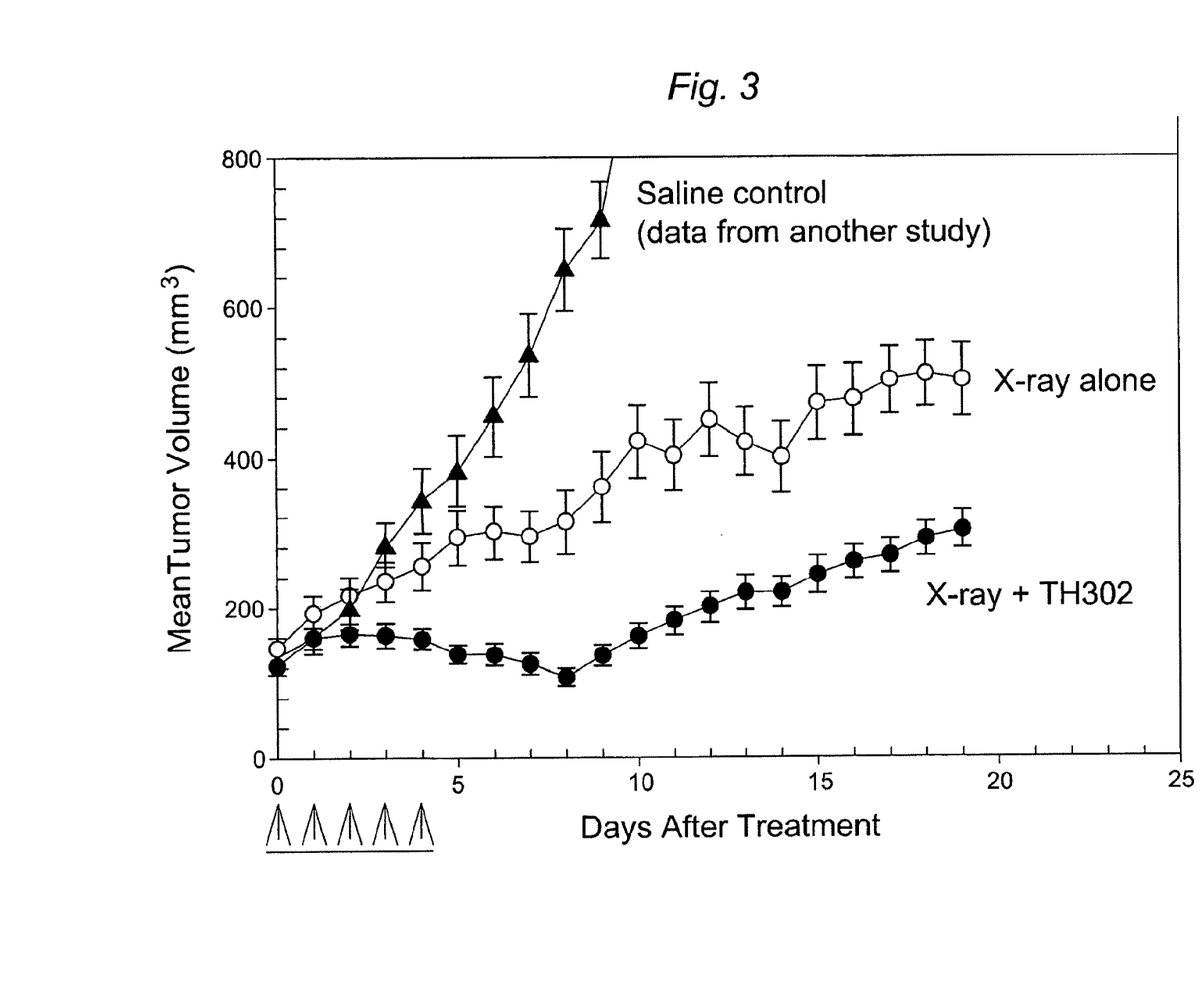
FIG. 3 demonstrates graphically that TH302, administered in combination with radiation, such as X-ray, enhances the anti cancer effect of X-ray in treating cancer in H460 xenograft tumor bearing mice. Arrows at the bottom of the graph indicate days on which drug and radiation were administered. See Example 9, infra.

H460 xenograft tumor bearing mice were treated with X-ray radiation (one cycle of 1.2 Gy/day for 5 days) alone and in combination with TH302 (administered ip, 75 mg/kg per day for 5 consecutive days 30 min after each radiation dose). Results are shown in FIG. 3. Without being bound by theory, radiation therapy is less effective in killing hypoxic tumor cells compared to normoxic tumor cells. The oxygen radicals involved in killing tumor cells, and which are generated by irradiation of oxygen e.g. under normoxic conditions, can not form efficiently under hypoxic conditions. Thus, this example demonstrates that, TH302 when administered in combination with radiation therapy for killing tumor cells, enhances the anti tumor efficacy of radiation for treatment of solid tumors.

Example 10

Demonstration of Safe Administration of TH302 to Rats and Dogs

A single-dose of TH302 was administered to rats and dogs over 30 min in order to achieve a rapid increase to relatively high drug levels. Rats were administered 50, 100, and 200 mg/kg, and dogs at 8, 16 and 32 mg/kg of TH302. Species specific toxicity at the highest dose was seen in the rat adipose and spleen. In both rats and dogs at the lowest toxicity level of the single dose studies, the primary findings were reduction in white blood cell counts accompanied only by moderate weight loss in male rats. These changes at the lowest toxicity level were fully reversible within 2 weeks. At the highest dose levels of 200 mg/kg in rats and 32 mg/kg in dogs, lethality was observed, affected organs in each species being bone marrow, kidney, thymus and intestine.

Based on these results, doses of 12.5, 25 and 50 mg/kg of TH302 were administered in a GLP multiple-dose toxicity study in rats. Each rat received a 30 minute infusion once a week for three weeks (Q7Dx3). The primary toxicities were hematologic in nature and were reversible. These effects were pronounced only at the highest dose (50 mg/kg) at which histopathology revealed effects on the bone marrow and the tongue with minor effects on the kidney and the uterus.

In the repeat dose GLP study with dogs, receiving 4, 8, and 16 mg/kg of TH-302, leucopenia and neutropenia were evident, particularly at the high dose level where hypocellularity was also reported in the bone marrow. These changes were reversible.

The minimally toxic doses were determined to be 25 mg/kg for the rat and 8 mg/kg for the dog. A rat dose can be converted to an estimated human equivalent dose by dividing the rat dose by 6.2. A dog dose can be converted to an estimated human equivalent dose by dividing the dog dose by 1.8. Therefore a 25 mg/kg rat dose corresponds to about 4 mg/kg human equivalent dose, and a dog dose of 8 mg/kg corresponds to about 4.5 mg/kg human equivalent dose.

As demonstrated in this example, in some other embodiments of the present invention, TH302 can be administered safely and therapeutically effectively to a human patient for treating cancer at a dose in the amount of about 0.1 mg/kg-about 40 mg/kg, about 0.2 mg/kg-about 20 mg/kg, about 0.4 mg/kg-about 10 mg/kg, or about 0.8 mg/kg-about 5 mg/kg for treatment of cancer in humans. In some other embodiments of the present invention, TH302 can be administered safely and therapeutically effectively to a human patient for treating cancer at a dose in the amount of about 0.1 mg/kg-about 10 mg/kg, about 0.2 mg/kg-about 5 mg/kg, about 0.4 mg/kg-about 3 mg/kg, and about 0.8 mg/kg-about 2 mg/kg for treatment of cancer in humans.

The therapeutically effective amount of an anti cancer agent can be expressed in units of mg/m$^2$. 1 mg/kg dose is equal to about 70 mg/patient. The estimated surface area of an average human patient is about 1.7 m$^2$. Thus, a 1 mg/kg or a 70 mg/patient dose is equal to about a 70/1.7 mg/m$^2$ or a 40 mg/m$^2$ dose. Therefore, an estimated human dose in mg/kg can be multiplied by 40 and be converted to a human dose in mg/m$^2$. Thus, in one embodiment, TH302 can be administered to human patients in a therapeutically effective amount of about 4 mg/m$^2$-about 1600 mg/m$^2$, about 8 mg/m$^2$-about 800 mg/m$^2$, about 16 mg/m$^2$-about 400 mg/m$^2$, and about 32 mg/m$^2$-about 200 mg/m$^2$. In another embodiment, TH302 can be administered to human patients in a therapeutically effective amount of about 4 mg/m$^2$-about 400 mg/m$^2$, about 8 mg/m$^2$-about 200 mg/m$^2$, about 16 mg/m$^2$-about 120 mg/m$^2$, and about 32 mg/m$^2$-about 80 mg/m$^2$.

A 25 mg/kg dose of TH302 in rats demonstrated a drug exposure measured by the AUC of TH302 of about 2110 h×nanogram (ng)/mL. An 8 mg/kg dose of TH302 in dogs demonstrated a drug exposure of about 1910 h×ng/mL (see data tabulated below). Therefore, in certain embodiments of the present invention, TH302 can be administered safely in humans for treatment of cancer wherein the exposure is about 500-about 14,000 h×ng/mL. The AUC measured for the active toxin, Br-IPM, was about 97 h×ng/mL in rats and about 21.8 h×ng/mL in dogs. Thus, in one embodiment, the present invention provides a method of treating cancer by administering a therapeutically effective amount of a prodrug of Br-IPM to a patient in need of such treatment, wherein said therapeutically effective amount of the prodrug of Br-IPM provides an AUC of about 10-1000 h×ng/mL of Br-IPM in plasma.

Table 1 shows pharmacokinetic parameters for TH302 determined on day 15 after repeated administration of TH302 (Q7Dx3) to rats according to Example 10.

TABLE 1

| Parameter | | Day 15 Dose (mg/kg): | | |
|---|---|---|---|---|
| | | 12.5 | 25 | 50 |
| $C_{max}$ | (µg/mL) | 1.21 | 3.64 | 5.72 |
| AUC | (µg-h/mL) | 0.699 | 2.11 | 3.25 |
| Half-Life | (h) | 0.266 | 0.312 | 0.346 |
| Cl | (L/h/kg) | 17.6 | 16.5 | 11.8 |
| $V_{ss}$ | (L/kg) | 8.71 | 8.28 | 5.84 |

Table 2 shows pharmacokinetic parameters for bromo-IPM (HO—P(=O)(NHCH$_2$CH$_2$Br)$_2$) determined after repeated administration of TH302 (Q7Dx3) to rats according to Example 10. Br-IPM being capable of reacting with water and a number of other nucleophiles, for HPLC analysis of Br-IPM, the plasma obtained was frozen and treated with NaF and potassium oxalate.

TABLE 2

| Parameter | | Day 15 Dose (mg/kg): | | |
|---|---|---|---|---|
| | | 12.5 | 25 | 50 |
| $C_{max}$ | (µg/mL) | 0.286 | 0.375 | 0.385 |
| AUC | (µg-h/mL) | 0.107 | 0.0970 | 0.143 |
| Half-Life | (h) | 0.148 | 0.138 | 0.383 |

Table 3 shows pharmacokinetic parameters for TH302 determined after after repeated administration of TH302 (Q7Dx3) to dogs according to Example 10.

TABLE 3

| Parameter | | Day 15 Dose (mg/kg): | | |
|---|---|---|---|---|
| | | 4 | 8 | 16 |
| $C_{max}$ | (µg/mL) | 1.58 | 3.65 | 7.10 |
| AUC | (µg-h/mL) | 0.853 | 1.91 | 4.26 |
| Half-Life | (h) | 0.271 | 0.253 | 0.284 |
| Cl | (L/h/kg) | 4.84 | 4.35 | 3.82 |
| $V_{ss}$ | (L/kg) | 2.10 | 1.78 | 1.93 |

Table 4 shows pharmacokinetic parameters for bromo-IPM (HO—P(=O)(NHCH$_2$CH$_2$Br)$_2$) determined after repeated administration of TH302 (Q7Dx3) to dogs according to Example 10.

TABLE 4

| Parameter | | Day 15 Dose (mg/kg): | | |
|---|---|---|---|---|
| | | 4 | 8 | 16 |
| $C_{max}$ | (µg/mL) | 0.00 | 0.0627 | 0.146 |
| $AUC_{last}$ | (µg-h/mL) | 0.00 | 0.0218 | 0.0607 |
| Half-Life | (h) | NC | NC | 0.305 |

Example 11

Demonstration of the Pharmacokinetics (PK) of TH302

Pharmacokinetic studies were performed in male CD-1 (50 mg/kg i.p. or orally (p.o.)) or female nude mice (50 mg/kg i.v. or i.p.), male Sprague-Dawley rats (1, 5, 20 and 50 mg/kg i.v. and 100 mg/kg, p.o.), beagle dogs (20 mg/kg, i.v.) and cynomologus monkeys (20 mg/kg i.v.). Plasma TH302 concentrations were analyzed using a LC/MS method and the pharmacokinetic parameters computed using a noncompartmental method. Interspecies scaling was performed according to standard methods. In CD-1 mice, plasma TH-302 concentrations declined with terminal half-lives ($t_{1/2}$) of 7.9 and 25.7 min and 91 min after 50 mg/kg i.p. and p.o., respectively, and with $t_{1/2}$ of 8.2 and 9.7 min after 50 mg/kg i.v. and p.o., respectively, in nude mice. The total body clearance (Cl) and apparent steady-state volume of distribution ($V_{ss}$) in nude mice was 4.37 L/h/kg and 0.542 L/kg, respectively. In rats, TH302 exhibited linear pharmacokinetics over the dose range studied. The mean terminal plasma $t_{1/2}$ ranged between 1.32-4.37 h following the i.v. dose. Mean Cl was high (4.69-6.14 L/h/kg) and mean $V_{ss}$ was large (1.67-5.09 L/kg). After p.o. dosing, TH302 was rapidly and substantially absorbed with mean peak plasma concentration reached at the first sampled time point of 15 minutes and an absolute oral bioavailability of 77.3%. The terminal plasma $t_{1/2}$ of TH-302 was 1.59 h.

After i.v. dosing in dogs, the mean Cl and $V_{ss}$ were 3.28 L/h/kg and 1.98 L/kg, respectively. The Mean $t_{1/2}$ was 49.2 min. In monkeys, TH302 had high Cl (7.66 L/h/kg) and a large $V_{ss}$ (2.92 L/kg). Plasma $t_{1/2}$ was 24.9 min. Interspecies scaling using a complex Dedrick analysis predicts a Cl and $V_{ss}$ of 109 L/h and 493 L for a 70-kg human. TH-302 demonstrated linear pharmacokinetics and excellent oral bioavailability. In all the species administered, TH-302 demonstrated a high Cl and large $V_{ss}$. The high clearance observed indicates that there may be an extrahepatic clearance pathway involved. Parts A, B, and C, below tabulate the pharmacokinetics of TH302 when administered to rats, Dogs, and monkeys.

A. Demonstration of TH302 PK in Rats

TH302 was dissolved in 50% PEG400/Saline to obtain a final concentration of 25 mg/mL, and then was further diluted to yield 25, 10, 2.5 and 0.5 mg/mL formulations of TH302 (pH The formulations were prepared just before dosing. The concentration of TH302 in dosing solution was confirmed by HPLC-UV. Male Sprague Dawley rats (body weight: 200 g to 230 g) were used in this study. Before the pharmacokinetic studies, animals were randomly assigned to four treatment groups cannulated in the carotid artery for serial blood sampling. All rats were administered a single intravenous bolus dose over one minute via the tail vein. The concentrations of TH302 in plasma were determined using a high performance liquid chromatography/mass spectrometry (HPLC/MS/MS) method. Following intravenous bolus administration at doses of 1, 5, 20 and 50 mg/kg, TH302 exhibited linear pharmacokinetics with a rapid distribution phase followed by a slower elimination phase. Results are tabulated below. The results demonstrated that, up to 8 mg/kg human equivalent daily dose, TH302 exhibited linear pharmacokinetics and that, the exposure of TH302, demonstrated by its AUC was about 8500.

TABLE 5

Pharmacokinetics Parameters of TH302 in Rats Following Intravenous Administration at Four Doses

| Animal Number | $AUC_{(0-t)}$ h × ng/mL | $AUC_{(0-\infty)}$ h × ng/mL | MRT h | $T_{1/2}$ h | $V_\beta$ L/kg | CL L/h/kg | $V_{ss}$ L/kg | $T_{max}$ h | $C_{max}$ ng/mL |
|---|---|---|---|---|---|---|---|---|---|
| (1 mg/kg) | | | | | | | | | |
| 1 | 202.22 | 203.34 | 0.69 | 2.18 | 15.45 | 4.92 | 1.49 | 0.03 | 732.20 |
| 2 | 174.91 | 178.44 | 0.95 | 1.75 | 14.19 | 5.60 | 1.83 | 0.03 | 682.78 |
| 3 | 273.70 | 282.01 | 1.03 | 2.16 | 11.03 | 3.55 | 2.82 | 0.03 | 990.12 |
| MEAN | 216.94 | 221.26 | 0.89 | 2.03 | 13.55 | 4.69 | 2.05 | 0.03 | 801.70 |
| SD | 51.01 | 54.06 | 0.18 | 0.24 | 2.27 | 1.05 | 0.69 | 0.00 | 165.04 |
| (5 mg/kg) | | | | | | | | | |
| 4 | 730.07 | 731.71 | 0.45 | 1.22 | 11.99 | 6.83 | 2.51 | 0.03 | 3841.30 |
| 5 | NA | NA | NA | NA | NA | NA | NA | 0.03 | NA |
| 6 | 868.22 | 919.39 | 1.36 | 6.29 | 49.33 | 5.44 | 7.68 | 0.03 | 3803.81 |
| MEAN | 799.15 | 825.55 | 0.90 | 3.75 | 30.66 | 6.14 | 5.09 | 0.03 | 3822.56 |
| SD | 97.69 | 132.71 | 0.64 | 3.58 | 26.40 | 0.99 | 3.66 | 0.00 | 26.51 |
| (20 mg/kg) | | | | | | | | | |
| 7 | 2831.37 | 2921.19 | 0.99 | 9.40 | 92.86 | 6.85 | 2.89 | 0.03 | 13431.30 |
| 8 | 3380.61 | 3387.13 | 0.41 | 1.08 | 9.16 | 5.91 | 2.29 | 0.03 | 12009.10 |
| 9 | 3597.80 | 3618.51 | 0.37 | 2.65 | 21.10 | 5.53 | 1.68 | 0.03 | 15053.50 |
| MEAN | 3269.93 | 3308.94 | 0.59 | 4.37 | 41.04 | 6.09 | 2.29 | 0.03 | 13497.97 |
| SD | 395.02 | 355.17 | 0.35 | 4.42 | 45.27 | 0.68 | 0.61 | 0.00 | 1523.29 |
| (50 mg/kg) | | | | | | | | | |
| 10 | 8827.84 | 8828.86 | 0.29 | 0.77 | 6.28 | 5.66 | 1.63 | 0.03 | 37198.50 |
| 11 | 8482.72 | 8488.15 | 0.30 | 0.94 | 7.99 | 5.89 | 1.68 | 0.03 | 37277.10 |
| 12 | 8083.24 | 8102.61 | 0.26 | 2.24 | 19.94 | 6.17 | 1.70 | 0.03 | 32033.40 |
| MEAN | 8464.60 | 8473.21 | 0.29 | 1.32 | 11.41 | 5.91 | 1.67 | 0.03 | 35503.00 |
| SD | 372.63 | 363.35 | 0.02 | 0.80 | 7.44 | 0.25 | 0.04 | 0.00 | 3005.02 |

B: Demonstration of the Pharmacokinetics of TH302 in Beagle Dogs

Pharmacokinetics of TH302 was demonstrated in dogs as tabulated below.

TABLE 6

|  | Females | | | | Males | | | |
| --- | --- | --- | --- | --- | --- | --- | --- | --- |
| Dose: (mg/kg) | 4 | 8 | 16 | 32 | 4 | 8 | 16 | 32 |
| Tmax (h) | 0.517 | 0.525 | 0.517 | 0.517 | 0.617 | 0.525 | 0.525 | 0.525 |
| Cmax (µg/mL) | 3.83 | 6.41 | 13.7 | 18.5 | 4.16 | 6.35 | 10.8 | 23.0 |
| AUC (µg·h/mL) | 2.27 | 3.40 | 7.66 | 9.53 | 2.33 | 3.64 | 6.20 | 11.0 |
| T½ (h) | 0.269 | 0.251 | 0.279 | 0.256 | 0.268 | 0.260 | 0.258 | 0.248 |
| Cl (L/h/kg) | 1.76 | 2.38 | 2.09 | 3.39 | 1.70 | 2.23 | 2.58 | 2.91 |
| Vss (L/kg) | 0.785 | 0.974 | 0.874 | 1.37 | 0.822 | 0.982 | 1.10 | 1.12 |

C: Demonstration of the Pharmacokinetics of TH302 in Cynomolgus Monkeys

Individual and mean pharmacokinetic parameters of TH302 following intravenous administration at a dose of 20 mg/kg (N=3) is shown in Table 7.

TABLE 7

| Animal | $T_{max}$ (h) | $C_{max}$ (ng/mL) | $AUC_{last}$ (ng × h/mL) | $T_{1/2}$ (ng × h/mL) | AUC (h) | MRT (h) | Cl (L/h/kg) | $V_\beta$ (L/kg) | $V_{ss}$ (L/kg) |
| --- | --- | --- | --- | --- | --- | --- | --- | --- | --- |
| 04C0075 | 0.033 | 15900 | 1519 | 1539 | 0.826 | 0.476 | 13.0 | 15.5 | 6.18 |
| 01C0597 | 0.033 | 28500 | 3961 | 4082 | 0.194 | 0.245 | 4.90 | 1.37 | 1.20 |
| 01C0379 | 0.033 | 17600 | 3932 | 3942 | 0.226 | 0.269 | 5.07 | 1.65 | 1.36 |
| Mean | 0.033 | 20667 | 3137 | 3188 | 0.415 | 0.330 | 7.66 | 6.17 | 2.92 |
| SD | 0 | 6837 | 1401 | 1429 | 0.356 | 0.127 | 4.62 | 8.07 | 2.83 |
| Min | 0.033 | 15900 | 1519 | 1539 | 0.194 | 0.245 | 4.90 | 1.37 | 1.20 |
| Max | 0.033 | 28500 | 3961 | 4082 | 0.826 | 0.476 | 13.0 | 15.5 | 6.18 |
| CV % | 0 | 33.1 | 44.7 | 44.8 | 85.7 | 38.4 | 60.4 | 131 | 97.0 |

Example 12

Demonstration of the Biodistribution of TH302

This example demonstrates the distribution of TH302 in vivo by whole body autoradiography (WBA) following administration of a single intravenous bolus dose of [$^{14}$C] TH302 to rats. Five male Sprague Dawley rats were assigned to one dose group. Non-radiolabeled TH302 (0.06 g) was weighed into an appropriate formulation bottle, a solution of 153 µL of [$^{14}$C] TH302 was measured and transferred to the formulation bottle, followed by the addition of 6.85 mL of 50 PEG400 in saline. The resulting formulation was cold-sterilized by filtration through a 0.22 µm mesh size commercial filter. The dosing formulation was kept at ambient temperature and in the dark pending dose administration. Animals were administered radiolabelled TH302 by intravenous injection of the formulation at a dose of 50 mg/kg wherein a radioactivity of about 100 µCi was administered. Following administration of TH302, the animals were sacrificed at selected time-points and carcasses were flash-frozen and processed for sectioning. A series of sagittal and para-sagittal sections were obtained from each carcass and were exposed to highly sensitive film until adequate imprinting of radioactivity was obtained. The pictures obtained were analyzed semi-quantitatively using computerized densitometry. The results demonstrated that following the intravenous administration of TH302, the radioactivity was associated with the gastro-intestinal (GI) tract, its contents, and the kidney.

Example 13

Phase I Clinical Trial of TH302 in Human Patients

This Example describes an open-label and multi-center Phase I trial administering TH302 to cancer patients.

Formulation and Administration of TH302

TH302 for injection (100 mg) was prepared in 100 mL glass vials. The product was a lyophilized cake and the vial was stoppered and crimp-sealed. TH302 was stored under controlled conditions at 2 to 8° C. Each dose was prepared in 250 mL of D5W and administered intravenously over 30 minutes via an infusion pump.

The amount and frequency of TH302 administration is as follows:

Level 1: 7.5 mg/m² weekly×3; 1 week rest
Level 2: 15.0 mg/m² weekly×3; 1 week rest
Level 3: 30.0 mg/m² weekly×3; 1 week rest A modified accelerated titration design is used (Simon et al., JNCI, 89:1138-47, incorporated herein by reference). Dosing is begun at Level 1. Up to two patients were to be enrolled at the initial dose levels. Until the first dose limiting toxicity (DLT) or Grade 2 toxicity that is clearly not related to disease progression, intercurrent illness, concomitant medications or other non-drug intervention occur during Cycle 1, the dose is increased 100% through successive levels. A DLT was defined as:

Grade 3 or Grade 4 non-hematologic toxicity (including febrile neutropenia),

Grade 3 or Grade 4 nausea, vomiting or diarrhea not able to be medically managed, Grade 4 neutropenia lasting >5 days, Grade 4 thrombocytopenia (or any requirement for platelet transfusion), Grade 4 anemia (unexplained by the underlying disease), any non-preexisting Grade 2 non-hematologic toxicity (excluding Grade 2 nausea, vomiting, diarrhea, alopecia and fatigue) which, in the judgment of the Investigator, medical monitor and sponsor, is considered a DLT, any Grade 2 or higher non-hematologic toxicity that does not resolve to Grade 0 or 1 toxicity by the start of the next cycle which, in the judgment of the Investigator, medical monitor and sponsor, is considered a DLT, or the inability to begin the next cycle of treatment within two weeks of the last dose due to unresolved toxicity.

Before proceeding to the next dose level, the medical monitor and the principal investigators were to review and discuss the available relevant safety and PK data.

Study Population

Up to 48 patients with advanced solid tumors will be enrolled in this study. Cohorts of up to 6 patients will participate in the modified accelerated titration dose escalation phase. Once the MTD has been established, 6 additional patients will be enrolled at the MTD dose level. The inclusion criteria are as follows:

1. At least 18 years of age
2. Ability to understand the purposes and risks of the study and has signed a written informed consent form approved by the investigator's IRB/Ethics Committee
3. Histologically or cytologically confirmed advanced or metastatic solid malignancy
4. Advanced or metastatic solid malignancy previously treated with one or more regimens of chemotherapy or for which no effective therapy available
5. Recovered from toxicities of prior therapy
6. Measurable disease by RECIST criteria (at least one target lesion)
7. ECOG performance status of 0 or 1
8. Life expectancy of at least 3 months
9. Acceptable liver function:
   Bilirubin≤1.5 times upper limit of normal
   AST (SGOT) and ALT (SGPT)≤2.5 times upper limit of normal (ULN); if liver metastases are present, then 5×ULN is allowed
10. Acceptable renal function:
    Serum creatinine ($S_{CR}$) within normal limits, OR calculated creatinine clearance ($CR_{CL}$≥60 mL/min/1.73 m$^2$ for patients with creatinine levels above institutional normal).
11. Acceptable hematologic status (without hematologic support):
    ANC≥1500 cells/μL
    Platelet count 100,000/μL
    Hemoglobin 9.0 g/dL
12. Urinalysis: No clinically significant abnormalities
13. Acceptable coagulation status:
    PT≤1.3×ULN
    PTT≤1.3×ULN
14. All women of childbearing potential must have a negative serum pregnancy test and women and men subjects must agree to use effective means of contraception (surgical sterilization or the use or barrier contraception with either a condom or diaphragm in conjunction with spermicidal gel or an IUD) with their partner from entry into the study through 6 months after the last dose.

The exclusion criteria will be as follows:

1. New York Heart Association (NYHA) Class III or IV, cardiac disease, myocardial infarction within 6 months prior to Day 1, or unstable arrhythmia
2. Seizure disorders requiring anticonvulsant therapy
3. Symptomatic brain metastases (unless previously treated and well controlled for a period of ≥3 months)
4. Severe chronic obstructive pulmonary disease with hypoxemia or in the opinion of the Investigator any physiological state leading to hypoxemia
5. Major surgery, other than diagnostic surgery, within 4 weeks prior to Day 1, without complete recovery
6. Active, uncontrolled bacterial, viral, or fungal infections, requiring systemic therapy
7. Treatment with radiation therapy, surgery, chemotherapy, targeted therapies (erlotinib, lapatinib, etc.) or hormones within 4 weeks prior to study entry (6 weeks for nitrosoureas or Mitomycin C)
8. Patients who participated in an investigational drug or device study within 28 days prior to study entry
9. Known infection with HIV, hepatitis B, or hepatitis C
10. Patients who have exhibited allergic reactions to a similar structural compound, biological agent, or formulation (containing solutol and/or propylene glycol)
11. Females who are pregnant or breast-feeding
12. Concomitant disease or condition that could interfere with the conduct of the study, or that would, in the opinion of the investigator, pose an unacceptable risk to the subject in this study
13. Unwillingness or inability to comply with the study protocol for any reason Screening Candidates will be evaluated for entry into the study according to the stated inclusion and exclusion criteria (Section 4, Study Population). The investigator will evaluate the results of all examinations, including clinical laboratory tests, and will determine each candidate's suitability for the study. The investigator must know the baseline results before enrollment. The serum pregnancy test for females of reproductive potential must be negative for those subjects to proceed to enrollment. All screening procedures were to be done within 21 days of Cycle 1/Day 1.

The following procedures will be performed to establish each candidate's general health and qualifications for possible enrollment into the study:

Medical history, including histology of primary tumor (and degree of differentiation), site of primary tumor, date of cancer diagnosis, date of diagnosis of advanced/metastatic disease, types and dates of prior anti-tumor therapy (including surgery, radiation therapy, systemic therapy), and date of most recent disease progression will be recorded. If previously treated, best response to last chemotherapy and date of progression will be recorded. If tumor measurements before and after chemotherapy are available, RECIST will be used for these tumor assessments. Recent medication history, including vitamins, herbal preparations, blood products, and other over the counter (OTC) drugs (including all concomitant medications taken within 14 days of Day 1) will be documented for enrolled subjects. 12-Lead ECG will be obtained. Blood pressure (BP), heart rate (HR), respiratory rate (RR) and temperature measurements will be recorded. These measurements will be done according to the standard instructions. A complete physical examination (including ocular assessment) will be performed, and height and weight recorded.

Perform tumor assessment with spiral CT scan of relevant location(s) (i.e., the abdomen, pelvis and/or chest plus other relevant evaluations to assess all known disease) within 28 days of study start and after completion of most recent antitumor therapy and after most recent progression. All known disease must be documented as target or non-target lesions using RECIST. Lesions that are expected to require palliative radiotherapy while on study should not be included as target lesions but should be listed as non-target lesions. Lesions that have not received radiotherapy in the previous 6 weeks may be target lesions.

Eastern Cooperative Oncology Group (ECOG) Performance Status will be assessed. Blood samples will be drawn for hematology and chemistry. Tumor markers will be obtained, if appropriate. Creatinine clearance (CrCL) will be calculate using the Cockcroft-Gault formula and standardized based on BSA:

Men: CrCL (mL/min/1.73 m$^2$)=(140−age)×(BW [kg])× (BSA)/(1.73×72×(serum creatinine [mg/dL])) where age is the age in years, BSA=body surface area (m$^2$), and BW (kg) is body weight Women: CrCL (mL/min/1.73 m$^2$)=0.85×(140−age)×(BW [kg])×(BSA)/(1.73×72×(serum creatinine [mg/dL]))

Serum HCG pregnancy test will be performed in female subjects of child-bearing potential (all female subjects unless surgically sterilized or at least 1 year post-menopausal). Urine samples will be for urinalyzed with micro.

Treatment Period:

Cycles 1-6: TH-302 will be administered weekly for 3 weeks followed by a 1 week rest period for up to 6 cycles. All required study assessments should be obtained within ±3 days of the nominal time point unless otherwise specified. Subjects must receive the first dose of study drug within 21 days of the start of screening.

The following procedures will be done in all subjects on day 1 of Cycle 1 before administering TH-302:

Cycle 1, Weeks 1, 2, and 3: A pre-dose blood and urine sample for PK analysis of TH-302 and Br-IPM will be collected (Week 1 and Week 3 only)

Cycles 1-6, Weeks 1, 2, and 3: Before TH-302 dosing, serum ALT, AST, bilirubin, creatinine, and calculated creatinine clearance should be evaluated. Creatinine clearance should be ≥60 mL/min/1.73 m$^2$ for TH302 administration. Before the first day of dosing on Cycle 1, ALT, AST, bilirubin and creatinine must meet protocol eligibility criteria within 3 days before administration of TH302.

Post-dose Plasma and Urine PK Procedures (Cycle 1 only): If the infusion is not completed in 30 minutes, the times of subsequent PK blood draws will be adjusted accordingly. Plasma and urine samples will be collected for PK analysis of TH-302 and Br-IPM. Concomitant medications will be recorded.

Dose Escalation

The size of the cohorts will be increased to a minimum of 3 subjects after the first DLT or Grade 2 drug-related toxicity that is clearly not related to disease progression, intercurrent illness, concomitant medications or other non-drug intervention beginning at the current dose level. Sequential cohorts of three patients will then treated with escalated doses until the MTD is established. Each dose escalation will be 20% to 40% greater than the previous dose with the percent increase dependent on the current dose level and the cumulative safety data. All subjects in a dose level cohort will be required to be followed for 4 weeks (or until DLT) before enrolling subjects at the next higher dose level. Dose escalations within individual patients will not be allowed.

After the observation of the first DLT or Grade 2 toxicity that is clearly not related to disease progression, intercurrent illness, concomitant medications or other non-drug intervention, at least 3 patients will be enrolled at each dose level. In the event that 1 of the first 3 patients at a dose level experiences a DLT, during the first cycle, up to 3 additional patients will be treated at that dose level. If 2 or more patients at a given dose level experience a DLT during the first cycle, then the MTD had been exceeded and up to a total of 6 patients will be treated at the next lower dose level. If fewer than 2 of 6 patients experiences a DLT at this next lower dose level, this dose will be declared the MTD.

Once an MTD has been established, 6 additional patients will be enrolled at the MTD dose level.

Dose Modifications

The dose modifications tabulated below will be allowed in individual patients. If it is necessary to delay a dose, the dose would be skipped and the patient would be given the next dose per schedule. If a patient requires more than 2 dose reductions for toxicity, the patient should discontinue treatment.

TABLE 8

TH302 Dose Modifications[1]

| Grade | Adverse Event | Action | Action after Resolution |
|---|---|---|---|
| Grade 1 toxicities | Creatinine clearance <60 mL/min/1.73 m$^2$ by Cockcroft-Gault | Hold dose and repeat CrCL at least 3 days later | Discontinue TH302 if CrCL remains <60 mL/min/1.73 m$^2$ |
| | Hematological (platelet count <100,000/uL) | Hold dose until platelet count ≥100,000/uL | Resume at full strength |
| Grade 2 toxicities[2] | All (except for alopecia, nausea, vomiting, diarrhea or fatigue) | Hold dose until resolution to Grade 0 or 1 | Resume at full strength |
| Grade 3 toxicities[3] | All (except for nausea and vomiting) | Hold dose until resolution to Grade 0 or 1 or until adequately treated (ie pulmonary embolism) | Resume at the previous lower dose level |
| Grade 4 toxicities | Life-threatening conditions that are considered to be due to TH-302 | Treatment should be discontinued | NA |
| | Other grade 4 events such as neutropenia, anemia, fatigue and non-life-threatening pulmonary embolism that are adequately treated | Hold dose until resolution to Grade 0 or 1 | Resume at the previous lower dose level if the treating physician determines that it is in the subject's best interest to continue |

[1]These guidelines are for adverse events that are considered to be not clearly related to disease progression, intercurrent illness, concomitant medications or other non-drug intervention. However, these dose modification rules were to be followed for all changes in CrCL and serum bilirubin, regardless of whether the abnormalities are considered to be not clearly related to disease progression, intercurrent illness, concomitant medications or other non-drug intervention. If a subject requires more than 2 dose reductions for toxicity, he/she should discontinue treatment.
[2]Gr. 2 ALT/AST at baseline, treatment should not be held if it remains Grade 2.
[3]Gr. 2 ALT/AST at baseline, treatment resumes when value returns to Grade 2.

Schedule of Assessments

The total duration of the active part of the study for each subject will be approximately 30 weeks, divided as follows:

Up to 3 weeks pre-dose (screening period); up to six 4-week cycles of treatment (24 weeks treatment period); optionally allowing subjects who have not progressed by the end of the treatment period to continue therapy on a case-by-case basis after review by the Investigator and Medical Monitor; safety follow-up period (study termination visit 1-2 weeks after the last dose of study medication); screening all subjects within 21 days prior to Cycle 1/Day 1 (Screening Visit).

Vital signs, clinical laboratory test results, weight and AEs will be used to assess safety. Efficacy will be assessed based on tumor assessments (objective response rate and duration of response) conducted at intervals during the study and overall survival.

Study Termination/Early Study Termination

If CrCL is abnormal (<75 mL/min/1.73 m² for females or <85 mL/min/1.73 m² for males) at study termination and at least 5 mL/min less than the value at Cycle 1/Day 1, serum creatinine must be measured and CrCL calculated once per 3 weeks until it returns to baseline or for 12 weeks, whichever comes first.

Pharmacokinetic Procedures

A blood sample for PK determination of plasma concentrations of TH-302 and/or Br-IPM will be collected in all subjects enrolled in the study on Days 1 and 15 of Cycle 1 only, pre-dose, 15 and 30 (end of infusion) 35, 45 minutes, 1, 1.5, 2, 2.5, 3.5, 4.5, 6.5, 8.5, and 12.5 hours post-start of infusion. If the infusion is not completed in 30 minutes, the times of subsequent PK blood draws should be adjusted accordingly. On Day 8 of Cycle 1, blood samples for PK analysis will be collected before dosing and at the end of the infusion.

Urine will be collected during the first 12 hours after dosing at the following time intervals: pre-dose, 0-4, 4-8 and 8-12 hours post-start of infusion for cycle 1 (Days 1 and 15) only.

Details on the collection, processing, storage, and shipment of plasma and urine samples will be provided in a separate manual.

Safety Procedures

A complete physical examination will be performed at screening and at study termination or early study termination. Limited physical examination will be done within 5 days before Week 1 treatment of Cycles 1-6. An ocular assessment will be performed with each complete and limited physical examination. If results of the ocular assessment are clinically significant, the patient should be referred to an ophthalmologist for further evaluation. A neurological exam will be performed with each complete and limited physical examination. Body weight will be measured prior to each dose. The results of the physical examinations will be used for safety monitoring purposes only. At each study visit, according to good medical practice, the subject's general health (eg, appearance, presence of illness or injury, temperature, and vital signs indicative of a concurrent illness) will be assessed to determine whether continued dosing is appropriate.

The maximum number of samples and approximate amount of blood to be collected from each subject are shown in Table 9.

TABLE 9

| Test | Screen | No. of Samples Cycle 1 | No. of Samples Cycle 2-6 | No. of Samples Cycle Term | Total No. of Samples | Approx. mL per Sample | Sub-total of Blood (mL) |
|---|---|---|---|---|---|---|---|
| Hematology | 1 | 3 | 15 | 1 | 20 | 5 | 100 |
| Serum chemistry | 1 | 3 | 15 | 1 | 20 | 5 | 100 |
| PT, PTT | 1 | 0 | 0 | 0 | 1 | 5 | 5 |
| Tumor Markers[1] | 1 | 1 | 5 | 1 | 8 | 5 | 40 |
| Plasma TH-302/Br-IPM | 0 | 30 | 0 | 0 | 30 | 5 | 150 |
| Serum pregnancy test[2] | 1 | 1 | 2 | 0 | 4 | 5 | 20 |
| Total mL blood | | | | | | | 415 |

[1]CA-125, CA 19-9, PSA, EGFR, Her-2, etc. and any other applicable cancer-specific tumor markers.
[2]Women of reproductive potential. Serum required at screening only. Urine or serum may be tested subsequently.

A total of approximately 415 mL of blood will be drawn from each subject during the study: 25 mL at screening, 290 mL during Cycle 1, 35-40 mL during each Cycle 2-6, and 15 mL at study termination. Blood samples will be used to assess clinical laboratory measurements and peak concentrations of TH-302 and Br-IPM.

While the present invention has been described with reference to the specific embodiments thereof, it should be understood by those skilled in the art that various changes can be made and equivalents can be substituted without departing from the scope of the invention. In addition, many modifications can be made to adapt a particular situation, material, composition of matter, process, process step or steps, to achieve the benefits provided by the present invention without departing from the scope of the present invention. All such modifications are intended to be within the scope of the claims appended hereto.

All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

The invention claimed is:

1. A pharmaceutically acceptable formulation suitable for intravenous administration comprising N,N'-bis(2-bromoethyl)phosphorodiamidic acid (1-methyl-2-nitro-1H-imidazol-5-yl)methyl ester (TH302) or a pharmaceutically acceptable salt thereof, and ethanol.

2. A unit dose of the pharmaceutically acceptable formulation of claim 1.

3. A method of treating cancer, said method comprising administering a formulation of claim 1 intravenously in an amount in the range of about 8 mg/m² to about 800 mg/m² to a human patient in need of such treatment.

4. The method of claim 3, wherein the TH302 is administered at a frequency of at least once per day to once per month.

5. The method of claim 4, wherein the TH302 is administered at a frequency of at least once per week.

6. The method of claim 3, wherein the TH302 is administered for a period of at least 1 week.

7. The method of claim 6, wherein the TH302 is administered for a period of at least 3 weeks.

8. The method of claim 7, wherein the TH302 is administered for a period of at least 24 weeks.

9. The method of claim 3, wherein the cancer treated is selected from the group consisting of breast cancer, colorectal cancer, pancreatic cancer, and prostate cancer.

10. The method of claim 3, wherein the cancer is a metastatic cancer selected from the group consisting of bone marrow cancer, lung cancer, liver cancer, lymph node cancer, and ovarian cancer.

11. The method of claim 3, wherein the TH302 is administered in combination with another anti cancer agent selected from the group consisting of cisplatin, carboplatin, docetaxel, paclitaxel, gemcitabine, and irinotecan, or is administered in combination with radiation therapy.

12. The method of claim 3, wherein the patient is also treated with docetaxel.

13. The method of claim 3, wherein the patient is also treated with irinotecan.

14. The method of claim 3, wherein the formulation contains not more than 5% of any solvent other than ethanol.

15. The method of claim 3, wherein TH302 is administered in an amount in the range of about 16 mg/m$^2$ to about 400 mg/m$^2$.

16. The method of claim 3, wherein TH302 is administered in an amount of at least 240 mg/m$^2$.

17. The method of claim 16, wherein cancer is colorectal cancer.

18. The method of claim 17, wherein irinotecan is administered in combination with TH302.

19. The method of claim 16, wherein the cancer is ovarian cancer.

20. The method of claim 16, wherein the cancer is lung cancer.

21. The method of claim 16, wherein the cancer is prostate cancer.

22. The method of claim 21, wherein docetaxel is administered in combination with TH302.

23. The method of claim 16, wherein the TH302 is administered in combination with radiation therapy.

24. The method of claim 23, wherein the cancer is lung cancer.

25. The method of claim 16, wherein the cancer is pancreatic cancer.

26. The method of claim 16, wherein the cancer is bone or soft tissue cancer.

27. The method of claim 26, wherein docetaxel is administered in combination with TH302.

* * * * *